(12) United States Patent
Khanna et al.

(10) Patent No.: US 7,452,690 B2
(45) Date of Patent: *Nov. 18, 2008

(54) PROTEASE EFC CELL SURFACE FUSION PROTEIN ASSAY

(75) Inventors: Pyare Khanna, Fremont, CA (US); Joseph L. Horecka, Fremont, CA (US)

(73) Assignee: DiscoveRx Corporation, Fremont, CA (US)

( * ) Notice: Subject to any disclaimer, the term of this patent is extended or adjusted under 35 U.S.C. 154(b) by 372 days.

This patent is subject to a terminal disclaimer.

(21) Appl. No.: 10/353,280

(22) Filed: Jan. 28, 2003

(65) Prior Publication Data

US 2004/0146956 A1 Jul. 29, 2004

(51) Int. Cl.
*C12Q 1/37* (2006.01)
(52) U.S. Cl. ............................. 435/23; 435/24; 435/14; 435/18; 435/4; 435/69.7; 435/69.8; 435/70.1; 435/173.4
(58) Field of Classification Search .................. 435/23, 435/24, 14, 18, 4, 69.7, 69.8, 70.1, 173.4
See application file for complete search history.

(56) References Cited

U.S. PATENT DOCUMENTS

| 5,223,393 | A | * | 6/1993 | Khanna et al. | 435/6 |
| 5,434,052 | A | * | 7/1995 | Khanna | 435/7.6 |
| 7,256,011 | B2 | | 8/2007 | Khanna | |
| 2003/0170770 | A1 | | 9/2003 | Khanna | 435/23 |
| 2004/0146956 | A1 | * | 7/2004 | Khanna et al. | 435/7.92 |
| 2005/0136488 | A1 | | 6/2005 | Horecka et al. | |

FOREIGN PATENT DOCUMENTS

| WO | WO 97/27320 | 7/1997 |
| WO | WO 98/42854 | 10/1998 |
| WO | WO 00/39348 | 7/2000 |

OTHER PUBLICATIONS

Eglen, R.M., Assay & Drug Dev. Tech., vol. 1(1), pp. 97-104, (Nov. 2002)(Abstract Only).*
Webster's II New Riverside University Dictionary, p. 946 (1994).*
Eglen, 2002, Assay and Drug Development Technologies, 1:1/97-104.
HitHunter Enzyme Fragment Complmentation, Cyclic-AMP Assay Kit DaTA Sheet, (Copyright 2001).

* cited by examiner

*Primary Examiner*—Chih-Min Kam

(57) ABSTRACT

Methods and reagents are provided for measuring protease activity. The reagent comprises a surface to which is linked an enzyme donor fragment through a protease recognition sequence, where the enzyme donor fragment complexes with an enzyme acceptor fragment to form an active indicator enzyme when the enzyme donor fragment is cleaved from said surface. Conveniently, the surface is a cell membrane surface where the reagent is expressed in the cell. The method comprises bringing together the reagent, the protease, the enzyme acceptor and substrate for the indicator enzyme and measuring the indicator enzyme activity as a measure of the protease activity. The method finds application in screening for compounds modulating the activity of the protease.

11 Claims, 4 Drawing Sheets

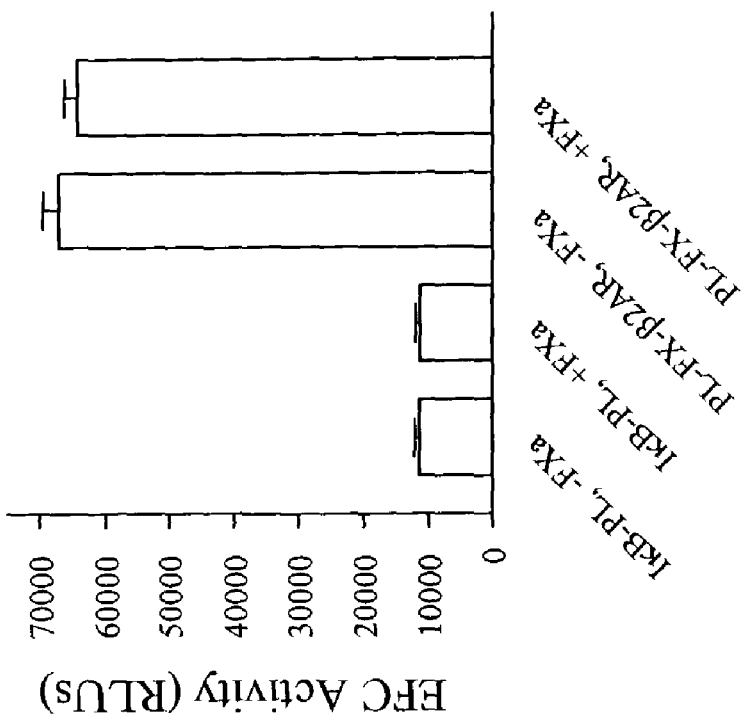
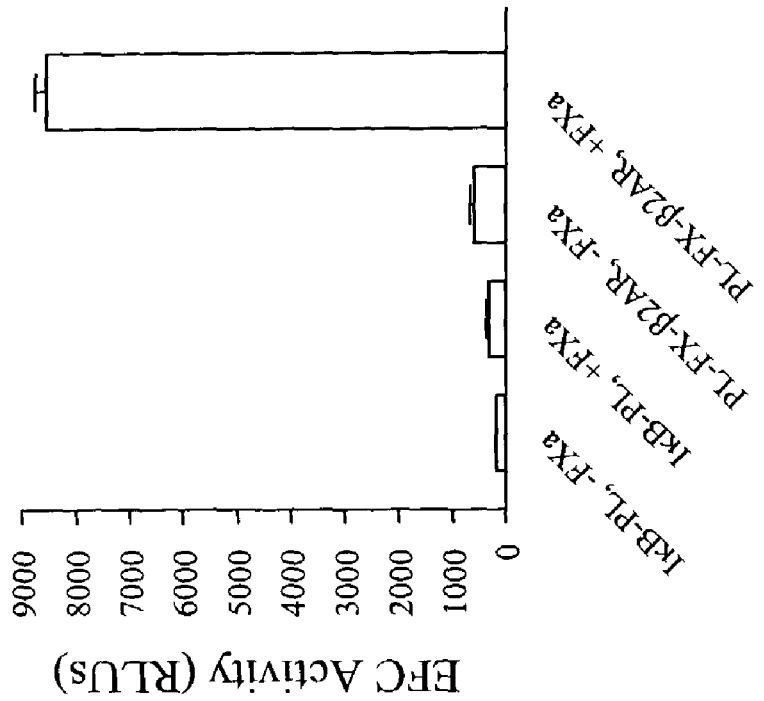

SEQUENCE LISTING

<160> NUMBER OF SEQ ID NOS: 10

<210> SEQ ID NO 1
<211> LENGTH: 4
<212> TYPE: PRT
<213> ORGANISM: artificial
<220> FEATURE:
<223> OTHER INFORMATION: protease cleavage site

<400> SEQUENCE: 1

```
Asp Glu Val Asp
1

<210> SEQ ID NO 2
<211> LENGTH: 4
<212> TYPE: PRT
<213> ORGANISM: Artificial
<220> FEATURE:
<223> OTHER INFORMATION: protease cleavage substrate

<400> SEQUENCE: 2

Asp Asp Val Asp
1

<210> SEQ ID NO 3
<211> LENGTH: 4
<212> TYPE: PRT
<213> ORGANISM: artificial
<220> FEATURE:
<223> OTHER INFORMATION: Protease cleavage site

<400> SEQUENCE: 3

Trp Glu His Asp
1

<210> SEQ ID NO 4
<211> LENGTH: 6
<212> TYPE: PRT
<213> ORGANISM: Artificial Sequence
<220> FEATURE:
<223> OTHER INFORMATION: Protease cleavage site

<400> SEQUENCE: 4

Lys Lys Arg Lys Arg Arg
1               5

<210> SEQ ID NO 5
<211> LENGTH: 10
<212> TYPE: PRT
<213> ORGANISM: Artificial Sequence
<220> FEATURE:
<223> OTHER INFORMATION: Protease cleavage site

<400> SEQUENCE: 5

Gly Ser Gly Ile Phe Leu Glu Thr Ser Leu
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Protease cleavage site

<400> SEQUENCE: 6

Val Pro Arg Gly Ser
1               5

<210> SEQ ID NO 7
<211> LENGTH: 4
<212> TYPE: PRT
<213> ORGANISM: Artificial Sequence
<220> FEATURE:
<223> OTHER INFORMATION: Protease cleavage site

<400> SEQUENCE: 7
```

```
Ile Glu Gly Arg
1

<210> SEQ ID NO 8
<211> LENGTH: 5
<212> TYPE: PRT
<213> ORGANISM: Artificial Sequence
<220> FEATURE:
<223> OTHER INFORMATION: Protease cleavage site

<400> SEQUENCE: 8

Asp Asp Asp Asp Lys
1               5

<210> SEQ ID NO 9
<211> LENGTH: 8
<212> TYPE: PRT
<213> ORGANISM: Artificial sequence
<220> FEATURE:
<223> OTHER INFORMATION: Protease cleavage site

<400> SEQUENCE: 9

Leu Glu Val Leu Phe Gln Gly Pro
1               5

<210> SEQ ID NO 10
<211> LENGTH: 16
<212> TYPE: PRT
<213> ORGANISM: Artificial sequence
<220> FEATURE:
<223> OTHER INFORMATION: Protease cleavage site

<400> SEQUENCE: 10

Met Lys Thr Ile Ile Ala Leu Ser Tyr Ile Phe Cys Leu Val Phe Ala
1               5                   10                  15
```

PROTEASE EFC CELL SURFACE FUSION PROTEIN ASSAY

BACKGROUND OF THE INVENTION

1. Field of the Invention

The invention relates generally to protease assays.

2. Background Information

Proteases play a vital role in the viability and regulation of cellular activity. Proteases act inter- and intramolecularly, to activate and inactivate proteins, and regulate expression of proteins by their action with transcription factors and transcription factor regulating proteins. Proteases are active in blood clotting and embolism dissolution, apoptosis, inflammatory activity, processing of proteins, metabolism, degradation of proteins, etc. The processes are greatly varied as to their action, mechanism and function. Proteases come within the class of hydrolases, hydrolyzing amide bonds. For this purpose, there are numerous classes of proteins, such as the serine/threonine hydrolases, metalloproteinases, cysteine proteases, etc. While many proteases are promiscuous in their recognition sequences, such as trypsin, chymotrypsin, bromelain, papain, etc., having fairly common recognition sites, many other proteases have recognition sequences that are rare except for the particular protease substrate.

In addition, there are many microorganisms that depend upon specific protease activity for their infectivity. Being able to inhibit proteases essential to the viability of the organism would diminish the infectivity of the organism. Viruses depend to a great degree on expressed proproteins that are cleaved to active products. Inhibiting such selective cleavage would inhibit the viability of the virus. There is, therefore, an interest in providing methods that can detect the presence of a specific protease in a sample, be capable of being used for rapid screening, be sensitive to the particular protease at low concentrations of the protease, while being reasonably stable to other proteases, and provide for a ready reliable readout.

Recently, in WO 00/39348 and references cited therein, a system is described that employs α-complementation between a small fragment of β-galactosidase called the enzyme donor fragment ("ED") and a larger fragment referred to as the enzyme acceptor ("EA"), where the two fragments complex to form an active β-galactosidase. The method described in the aforementioned application fuses the ED to a protein of interest, where there is a recognition sequence in the protein of interest. The fusion protein is reported to have substantially less activity than the protease catalyzed product. This method has numerous deficiencies. One of the advantages of the ED use in the appropriate environment is that it is readily degraded intracellularly, so that ED, by itself, does not provide a background. Where the ED is cleaved from the protein of interest, it may be rapidly degraded, so as to confuse the result. Furthermore, the inhibition of complexing of ED to EA is difficulty achieved, so that the fusion protein will have significant activity. Since initially the fusion protein will be present in much greater amount than the cleavage product, one will be dealing with small differences in observed signal, substantially reducing the sensitivity of the assay.

One of the issues associated with assays is the preparation of reagents in pure form. Frequently, purification can be difficult since impurities can lead to background interference with the assay, inhibitors of enzymes or other interfering aspects. In addition, purification can substantially add to costs, where there is reduction in the amount of product, the cost of the purification protocol and the requirement for quality analysis. There is great interest in devising ways to reduce the cost of reagents and avoid purification and quality control.

RELEVANT LITERATURE

WO 00/039348, as indicated above, describes a protease assay where the marker is a β-galactosidase fragment fused to a protein having a specific protease cleavage site. There are numerous other references concerned with the use of β-galactosidase fragments in assay systems. The following are illustrative. Douglas, et al., Proc. Natl. Acad. Sci. USA 1984, 81:3983-7 describes the fusion protein of ATP-2 and lacZ. WO92/03559 describes a fusion protein employing α-complementation of β-galactosidase for measuring proteinases. WO01/0214 describes protein folding and/or solubility assessed by structural complementation using the α-peptide of β-galactosidase as a fusion protein. WO01/60840 describes fusion proteins including a fusion protein comprising an enzyme donor β-galactosidase for measuring protein folding and solubility. Homma, et al., Biochem. Biophys. Res. Commun., 1995, 215, 452-8 describes the effect of α-fragments of β-galactosidase on the stability of fusion proteins. Abbas-Terki, et al., Eur. J. Biochem. 1999, 266, 517-23 describes α-complemented β-galactosidase as an in vivo model susbtrate for the molecular chaperone heat-shock protein in yeast. Miller, et al., Gene, 1984, 29, 247-50 describe a quantitative β-galactosidase α-complementation assay for fusion proteins containing human insulin β-chain peptides. Thomas and Kunkel, Proc. Natl. Acad. Sci. USA, 1993, 90, 7744-8 describe an ED containing plasmid to measure mutation rate.

SUMMARY OF THE INVENTION

Fusion protein reagents are provided bound to a surface, usually cellular, comprising an enzyme complementation fragment ("enzyme donor") bound to the membrane through a protease recognition site. The fusion protein reagent has a low complexing capability when combined with the complementary fragment ("enzyme acceptor") so as to provide low background. The cells are modified for expression of the fusion protein to provide the fusion protein in a reactive form to the protease while bound to the surface. In performing the assay, the cells are combined with the protease, EA and a substrate that provides a detectable signal, the assay mixture incubated, and the signal read. By adding to the assay a candidate compound for modulating protease activity, a change in signal can be related to the modulating activity of the candidate compound.

BRIEF DESCRIPTION OF THE DRAWINGS

FIGS. 1a and 1b are bar graphs showing the results of assays employing a supernatant fraction (1a) and an adherent fraction, where the former is not lysed and the latter is lysed;

DETAILED DESCRIPTION OF THE INVENTION

Figure 2:
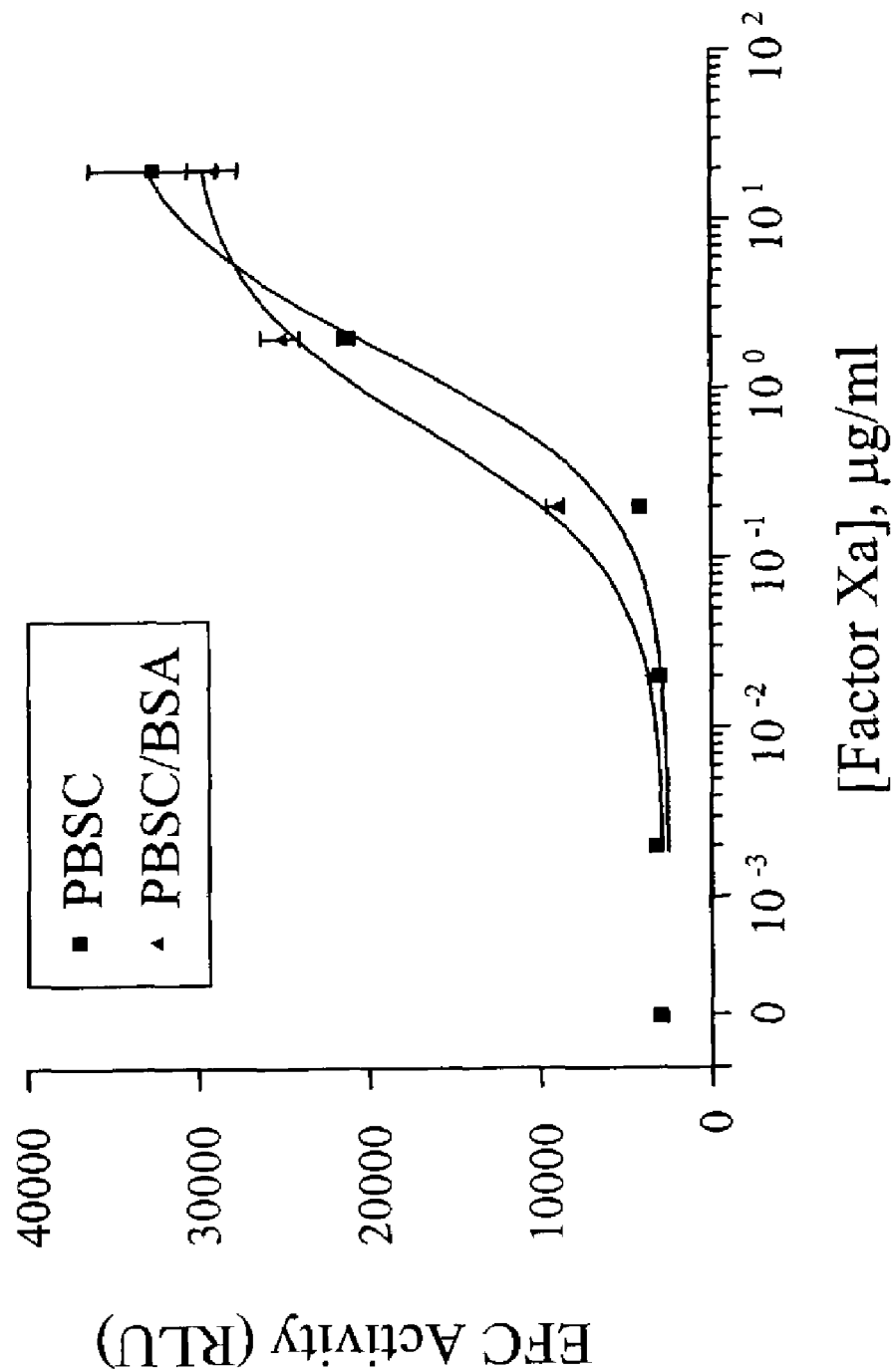
FIG. 2 is a plot of the effect of FXa concentration on the observed signal in two different buffers with an expression construct comprising ProLabel (ED)

Protease assays are provided, particularly for screening candidate compounds that modulate protease activity. The assays for the most part employ modified cells to which have been added expression constructs that express a fusion protein that is transported to the cellular membrane and bound to the membrane, where the membrane provides a surface hindering entity. The fusion protein comprises N-proximal a component of an enzyme fragment complementation pair ("enzyme donor") linked to the membrane-binding component through a protease recognition site that has upon cleavage sufficient size as to be substantially stable under the conditions of the assay. The modified cells have a low affinity for forming an active enzyme complex with the complementary member of the enzyme fragment complementation pair ("enzyme acceptor") so as to provide a low background signal. The assay is performed by combining the fusion protein, usually associated with cells, protease, the enzyme acceptor, a substrate that provides a detectable signal, and optionally the candidate compound, and the signal measured. A difference in signal between the results in the presence and absence of the candidate compound indicates that the candidate compound is active in modulating the activity of the protease.

In describing the subject invention, the cells will be considered first in conjunction with the constructs used to modify the cells, followed by the enzyme fragment complementation pair, followed by a description of the assay and its components.

Any prokaryotic or eukaryotic cell may be employed, preferably eukaryotic and more preferably from a vertebrate source. The cells will usually be established cell lines and may be from any convenient host and organ, including murine, bovine, canine, feline, mammalian, e.g. human, porcine, lagomorpha, etc. Organs may include ovary, neuronal, epithelial, endothelial, hematopoietic, muscle, etc. The particular cells will be a matter of convenience as to maintenance, stable expression, ease of transformation, presence of the means for binding the fusion construct to the membrane, performance in the assay and the like. At the time of use of the cells, the cells may be viable or non-viable.

The fusion DNA construct encoding the protein reagent will usually have the following formula:

$$(CC)_a\text{-MBC-L-RS-L-ED-}(SC)_b\text{-}(LS)_c$$

wherein:

LS is a leader sequence;

CC is the cytoplasmic component:

a and b are 0 or 1 intending that there may or may not be a designated component;

c is 0 or 1, the leader sequence being optionally present when the membrane binding component comprises a leader sequence providing for the ED to be extracellular;

MBC is the membrane binding component;

L is a bond or amino acid linker of from 1 to 30, generally from 1 to 20, and frequently from 1 to 10 amino acids;

RS is the protease recognition sequence and may vary from as few as 4 to as many as about 50 amino acids;

ED is the enzyme donor fragment and will usually be within 75, more usually within 50 amino acids of MBC; and SC is a stabilizing component to stabilize ED from protease degradation, if proteases are present in the assay medium, generally being a poly(amino acid) of from about 5 to 50 kDa, usually from about 10 to 35 kDa.

LS is the leader sequence and may be any convenient leader sequence that guides the fusion protein through the cell membrane. Where there is an internal leader sequence that suffices for anchoring the extracellular portion of the fusion protein to the membrane, there need be no terminal leader sequence. Numerous proteins that are secreted or membrane bound are known and the leader sequence may be greatly varied as to the sequence without affecting the functionality of the leader sequence. The leader sequence generally is about 18 to 25 amino acids having about 2 polar amino acids at each terminus and neutral and substantially non-polar amino acids bridging the polar amino acids. Where a naturally occurring protein is used to anchor the fusion protein, the leader sequence of such protein can be used, inserting the other functional components between the leader sequence and the remaining portion of the protein. Alternatively, where the stabilizing component SC is present and is a natural protein that has a leader sequence, then this leader sequence will suffice. Natural leader sequences may be obtained from interleukins, such as IL-1α, IL-1β, L-4, etc., basic fibroblast growth factor (bFGF), EGF receptor, insulin receptor, glucose transporter, NGF receptor, and endothelial-monocyte activating peptide, as illustrative. Where there is no natural leader sequence, the polynucleotide encoding such sequence can be added at the end of the gene encoding the fusion protein. The manner of providing the leader sequence is conventional and need not be expanded upon here.

The CC or cytoplasmic component, if present, will usually be part of the protein that is used to anchor the fusion protein in the membrane. Where a stop code sequence (stopping continued transfer of the protein through the membrane) is employed, there will usually be a cytoplasmic tail, where the length of the tail is not critical to the subject invention, generally being under about 200, usually under about 100 amino acids. The protein may pass through the membrane one or more times, the number of times not being germane to the subject invention. While the protein may complex with other species in the cytoplasm, this also is not relevant to the subject invention, as such events are shielded from the extracellular portion of the fusion protein. Conveniently the cytoplasmic portion may come from various receptors whose genes are conveniently available, such as β-andrenergic receptor, major histocompatibility complex protein, insulin receptor, adhesion protein, hormone receptor, growth factor receptor, etc.. Alternatively there need not be a cytoplasmic portion where the membrane-binding component, MBC, is a lipid that is inserted into the cell membrane. Various coding sequences provide for post-expression processing, providing for attachment of a lipid group that becomes inserted into the cell membrane and retains the fusion protein bound to the cell membrane.

The MBC, as already discussed in conjunction with the cytoplasmic component, can be an amino acid sequence spanning the cell membrane or a lipid group inserted into the cell membrane. The membrane spanning sequence is analogous to the leader sequence in its composition and size and is conveniently part of the protein used for the preparation of the fusion protein. For receptors, it will inherently be present in the protein and need not be additionally provided. Alternatively, one may provide for lipid attachment to the fusion protein by providing for an appropriate sequence that encodes for farnesylation, myristoylation, etc. These sequences encoding for post-translational processing are well known and are described in numerous texts and articles. See, for example, Reuther, et al., 2000 Meth Enzymol 327, 331-50; van't Hoff and Rich, 2000 ibid 327, 317-330; and Hofemeister, et al. 2000 Mol Cell Biol 11, 3233-46.

The MBC will hold the ED in sufficient spatial proximity to provide hindering of the ED to form a complex with EA. Thus, the lipid surface acts to hinder the formation of the active enzyme complex, so that the ED is substantially inactive even in the presence of excess EA.

The linker, L, if present may be comprised of any of the naturally occurring amino acids, although linkers will be prepared that are neither too hydrophobic, too hydrophilic, nor too charged. For the most part the small amino acids of fewer than 6 amino acids will be used and charged amino acids will be limited to not more than 3, usually not more than 2 in a linker. Desirably, the neutral polar amino acids can be used, such as threonine, serine and methionine. Cysteine will usually be avoided.

The RS will be associated with specific proteases or classes of proteases. The target proteases of interest are for the most part those that have specific recognition sequences, preferably having at least about 4 amino acids as their recognition sequence and usually not more than about 12 amino acids, although additional amino acids may be involved in enhancing the recognition by the protease. As indicated, the protease may be an intra- or intermolecular protease, where in the former case, the protease will require activation before self-cleavage, usually requiring another enzyme or cofactor to activate the protease. For this purpose the CC-MBC-L would form the self-cleaving protease. However, this is a rare situation and for the most part the proteases will be intermolecular proteases, where the recognition site is part of a protein different from the protease. The recognition sequence may be one or more than one recognition sequence for the same or different protease, so that a single construct may suffice for a plurality of proteases. In effect, the protease recognition sequences that are not employed in the assay would serve as linkers.

Enzymes of interest include serine/threonine hydrolases, cysteine hydrolases, metalloproteases, BACEs (e.g., α-, β- and γ-secretases). Included within these classes are such protein groups as caspases, the individual MMPs, elastases, collagenases, ACEs, carboxypeptidases, blood clotting related enzymes, complement components, cathepsins, dipeptidyl peptidases, granzymes, etc. For other enzyme groups, see Handbook of Proteolytic enzymes, ed. A J Barnet, N D Rowland, and J F Woessner. Other types of enzymes include abzymes.

Specific serine proteases include neutrophil elastase, involved in pulmonary emphysema, leukocyte elastase, tyrosine carboxypeptidase, lysosomal carboxypeptidase C, thrombin, plasmin, dipeptidyl peptidase IV; metalloproteinases include carboxypeptidases A and B, angiotensin converting enzyme, involved in hypertension, stromelysin, involved with inflammatory disorders, e.g. rheumatoid arthritis, P. aeruginosa elastase, involved in lung infections; aspartic proteases include renin, involved in hypertension, cathepsin D, HIV protease; cysteine proteases include lysosomal carboxypeptidase, cathepsin B, involved in cell proliferative disorders, cathepsin G, cathepsin L, calpain, involved with brain cell destruction during stroke; etc.

The proteases may be involved with various processes, such as infections and replication of the infectious agent, viral, bacterial, fungal, and protista; phagocytosis, fibrinolysis, blood clotting cascases, complement cascades, caspase cascades, activation of proforms of proteins, protein degradation, e.g. ubiquitinated proteins, apoptosis, etc., cell growth, attachment, synaptic processes, etc. The proteases may come from a variety of sources, either prokaryotes, eukaryotes or viruses, depending on the nature of the assay. For detection of infectious diseases, the source of the protease may be a virus, a bacterium, protista, fungus or other unicellular organism. For higher orders of species, the enzyme may be derived from plants, non-vertebrates, vertebrates, particularly mammals, such as domestic animals, e.g. bovine, porcine, canine, feline, lagomorpha, murine, etc., primates, e.g. humans.

The purpose of measuring the protease will be widely varied. In some instances, one will be concerned with identifying the source, such as a virus, where the protein reagent will comprise a viral protein recognition sequence specifically cleaved by the protease. In other cases, one may be interested in the presence of the protease in a biological sample, determining whether the protease is present and in what concentration. One will also be interested in determining the amount or change in amount of protease in response to changes in the nature of the cell, e.g. normal and cancerous, or in response to a change in environment, e.g. physical or chemical environment, native or diseased state, e.g. infection, or the like. The subject system is particularly useful for high throughput screening of drug candidates, as to their effect on the target protease or non-target proteases.

As already indicated, the organisms from which the proteases are naturally derived are varied. Among viruses, the proteases may be derived from HIV-1, and -2, adenoviruses, hepatitis viruses, A, B, C, D and E, rhinoviruses, herpes viruses, e.g. cytomegalovirus, picomaviruses, etc. Among unicellular microorganisms are Listeria, Clostridium, Escherichia, Micrococcus, Chlamydia, Giardia, Streptococcus, Pseudomonas, etc. Of course, there are numerous mammalian proteases of interest, particularly human proteases.

There are numerous scientific articles describing proteases and their substrates. Illustrative articles are as follows, whose relevant content is specifically incorporated herein by reference. Among the metalloproteinases are MMP-2, having target sequences L/IXXXHy; XHySXL; and HXXXHy (where Hy intends a hydrophobic residue), Chen, et al., J. Biol. Chem., 2001; Other enzymes include mitochondrial processing peptidase, having the target sequence RXXAr (where Ar is an aromatic amino acid), Taylor, et al., Structure 2001, 9, 615-25; caspases, VAD, DEVD (SEQ ID NO: 1) and DXXD, as well as the RB protein, Fattman, et al., Oncogene 2001, 20, 2918-26, DDVD (SEQ ID NO: 2) of HPK-1, Chen, et al., Oncogene 1999, 18, 7370-7; VEMD/A and EVQD/G of Keratins 15 and 17, Badock, et al., Cell Death Differ. 2001, 8, 308-15; WEHD (SEQ ID NO: 3) of pro-interleukin-1β, Rano, et al., Chem. Biol. 1997, 4, 149-55; furin, KKRKLRR (SEQ ID NO: 4) of RSV fusion protein, Zimmer, et al., J. Biol. Chem. 2001, 20, 2918-26; HIV-1 protease, GSGIF*LETSL, (SEQ ID NO: 5) Beck, et al., Virology 2000, 274, 391-401. Other enzymes include thrombin, VPRGS, (SEQ ID NO: 6) Factor Xa protease, IEGR (SEQ ID NO: 7), enterokinase, DDDDK, (SEQ ID NO: 8) 3C human rhinovirus protease, LEVLFQ/GP (SEQ ID NO: 9).

Other references describing proteases include: Rabay, G. ed., "Proteinases and Their Inhibitors in Cells and Tissues, 1989, Gustav Fischer Verlag, Stuttgart; Powers, et al., in "Proteases-Structures, Mechanism and Inhibitors," 1993, Birkhauser Verlag, Basel, pp.3-17; Patick and Potts, Clin. Microbiol. Rev. 1998, 11, 614-27; Dery, et al., Am. J. Physiol. 1998, 274, C1429-52; Kyozuka, et al., Cell Calcium 1998, 23, 123-30; Howells, et al., Br. J. Haematol. 1998, 101, 1-9; Hill and Phylip, Adv. Exp. Med. Biol. 1998, 436, 441-4; Kidd, Ann. Rev. Physiol. 1998, 60, 533-73; Matsushita, et al., Curr. Opin. Inmunol. 1998, 10, 29-35; Pallen and Wren, Mol. Microbiol.1997, 26, 209-21; DeClerk, et al., Adv. Exp. Med. Biol. 1998, 425, 89-97; Thomberry, Br. Med. Bull. 1997, 53, 478-90, which references are specifically incorporated herein.

Besides the naturally occurring recognition sequences, using combinatorial approaches, one can design recognition sequences that will have specificity for one or a family of enzymes. By preparing a library of oligopeptides that are labeled and having an array of the labeled oligopeptides where the location identifies the sequence, one need only add the protease of interest to the array and detect the release of the label. Having microwell plates, with the oligopeptides bound to the surface and labeled with a fluorescer, allows one to follow cleavage by internal reflection of activating irradiation. Numerous other approaches can also be used. By using synthetic sequences, one can optimize the cleavage for a particular protease. By using a plurality of protein reagents, one can obtain profiles that will be specific for specific enzymes.

The ED will be a fragment of an enzyme that can be complemented with another fragment, the EA, to form an active enzyme. There are two different situations. In a first situation, the ED and EA complex to form the active enzyme in the absence of any ancillary binding. The ED and EA individually are substantially inactive, but when combined independently complex to form the active enzyme. In the other situation, the fragments of the enzyme are fused to polypeptides that independently complex, and when the auxiliary polypeptides complex, the enzyme fragments complex to form an active enzyme. As in the first situation, the enzyme fragments are substantially inactive individually, but as distinguished from the first case, when the two enzyme fragments are brought together in the absence of the auxiliary polypeptides, the fragments do not complex to form an active enzyme The indicator enzymes formed by the ED and EA and their ED and EA fragments are required to have a number of characteristics. The fragments should be substantially inactive, in that there should be little, if any, background with only one fragment present in the presence of substrate. Secondly, the fragments have sufficient affinity for each other, so that upon scission of the surface from a fragment of the protein reagent, the fragments will combine to provide an active enzyme. The ED fragment of the protein reagent will complex with the EA fragment as a result of the affinity of the fragments of the enzyme for each other or as a result of being fused to auxiliary binding entities that will bring the enzyme fragments together resulting in an active enzyme. That is, in the former case, the enzyme fragments are capable of complexing without having an auxiliary binding entity to bring the fragments together to form a complex. In the latter case, the enzyme fragments will not independently form a complex, but when the auxiliary proteins form a complex, the enzyme fragments are then able to form an active enzyme.

Various indicator enzymes are known that fulfill these criteria and additional enzymes may be developed in accordance with known technologies. Indicator enzymes that fit these criteria include β-galactosidase (See, U.S. Pat. No. 4,708,929), ribonuclease A (See, U.S. Pat. No. 4,378,428), where the smaller fragment may come from the amino or carboxy terminus, β-lactamase WO 00/71702 and 01/94617 and Wehrman, et al., Proc. Natl. Acad. Sci. 2002, 99, 3469-74, or enzymes that have small peptide cofactors, such as adenovirus proteases (See, U.S. Pat. No. 5,935,840). To identify other indicator enzymes that can serve in place of the above indicator enzymes, enzyme genes may be cleaved asymmetrically to define a small and large fragment and expressed in the same and different cells. In the presence of the substrate, the cells producing both fragments would catalyze the reaction of the substrate, while there should be little, if any turnover, with the individual fragments. Alternatively, one may express the fragments individually and if there is no reaction, combine the mixtures to see whether an enzyme-catalyzed reaction occurs.

Indicator enzymes of interest are those that are below about 300 kDa, generally below about 150 kDa. The independently complexing small fragment will be under 15 kDal, more usually under about 10 kDal, frequently under about 125 amino acids, generally under about 100 amino acids and preferably not more than about 75 amino acids. Depending on the enzyme the independently complexing ED may be as small as 10 amino acids, usually being at least about 25, more usually at least about 35amino acids. With this criterion in mind, the fragments that are screened can be selected to provide the appropriately sized small fragment.

The enzymes having fragments that complex in conjunction with a fused auxiliary protein will generally have fragments having from 20-80, more usually 25-75% of the amino acids of the enzyme. The fragments may be modified by the addition of from about 1 to 20, usually 2 to 10, amino acids to enhance the affinity of the fragments during complexation. Enzymes that provide for low affinity complexation to an active enzyme include β-galactosidase, β-glucuronidase, Staphylococcal nuclease, and β-lactamase, as exemplary. The binding proteins may have as few as 8, more usually at least 10 amino acids and may be 150, usually not more than about 100 kDal. Binding proteins may include homo- and heterodimers, epitopes and immunoglobulins or fragments thereof, e.g. Fab, ligands and receptors, etc. In some instances, complexation may require the addition of an additional reagent, so that complexation with formation of an active enzyme does not occur to any significant degree in the absence of the additional reagent, e.g. FK1012, cyclosporin and rapamycin.

Each of the indicator enzymes will have an appropriate substrate. β-galactosidase uses effectively fluorescers having phenolic groups that are etherified with a β-galactosyl group or oxetanes having galatosidyl substitution for chemiluminescence. Ribonuclease A, fluorescer modified nucleotides, exemplified by 5'-O-acetyl 2'-O-(tetrahydropyran-2-yl)uridine 3'-(4-methylumbelliferon-7-yl)ammonium phosphate, adenovirus proteinase, -(L, I, M)-X-G-G/X- or -(L, I, M)-X-G-X/G-, where the vertical line denotes the position of cleavage; the P3 (X) position appears to be unimportant for cleavage (Anderson, C. W., Virology, 177;259 (1990); Webster, et al., J. Gen. Virol., 70;3225 (1989)) and the peptide substrate can be designed to provide a detectable signal, e.g. using fluorescence resonance energy transfer, by having a fluorescer and a quencher on opposite sides of the cleavage site. β-Glucuronidase substrates are exemplified by 5-Br-4-Cl-3-indolyl β-D-glucuronidase.

Since β-galactosidase is paradigmatic of the peptides used in the subject invention, demonstrating the criteria for having two peptides that when combined complex non-covalently to form an active enzyme, this enzyme will be frequently referred to hereafter as illustrative of the class, except for those situations where the different enzymes must be considered independently. The ED for β-galactosidase is extensively described in the patent literature. U.S. Pat. Nos. 4,378,428; 4,708,929; 5,037,735; 5,106,950; 5,362,625; 5,464,747; 5,604,091; 5,643,734; and PCT application nos. WO96/19732; and WO98/06648 describe assays using complementation of enzyme fragments. The β-galactosidase ED will generally be of at least about 35 amino acids, usually at least about 37 amino acids, frequently at least about 40 amino acids, and usually not exceed 100 amino acids, more usually not exceed 75 amino acids. The upper limit is defined by the effect of the size of the ED on the performance and purpose of the determination, the activity of the fragment and the complex, and the like.

The stabilizing component, SC, if present, may be somewhat arbitrarily chosen, although there are some constraints. The SC should be relatively small, between about 5 and 50 kDa, usually 10 and 40 kDa, should be soluble, should not interfere with the activity of the ED or the recognition site, and should not affect the activity of the protease. SCs will generally be used when the ED is small and the linker is small, so that there is the opportunity for degradation in the assay mixture. Generally, the ED that is less than about 120, usually less than about 100 amino acids will be accompanied after cleavage with either the SC or sufficient amino acids from the linker and the residue of the RS to provide a stable ED fragment.

The fragment that is released should comprise at least about 125 amino acids, more usually at least about 150 amino acids and not more than about 300 amino acids for the independently complexing fragment and may be 500 or more amino acids for the non-independently fusion protein fragments. Stability of the small fragments are greatly enhanced by having a protein that is stable to degradation, which is achieved by having amino acids additional to the ED, particularly the smaller independently complexing EDs. A gene for the fusion protein will be constructed with the 5' terminus having the sequence encoding the cytoplasmic portion, if present, or the membrane binding component, while the 3' terminus will have the stabilizing component, if present, or the enzyme donor sequence.

The expression construct is produced in accordance with conventional ways, as described in various laboratory manuals and by suppliers of vectors that are functional in numerous hosts. See, for example, Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach,"Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Vectors that may be used include viruses, plasmids, cosmids, phagemids, YAC, BAC and HAC. Other components of the vector may include origins of replication for one or more hosts, expression constructs for selection, including antibiotic resistance, proteins providing for a signal, etc., integration sequences and enzymes providing for the integration, multiple cloning sites, expression regulatory sequences, expression construct for a protein of interest, particularly where the protein is coordinately or differentially expressed in relation to the protein reagent, sequences allowing for ready isolation of the vector, etc. Commercially available vectors have many or all of these capabilities and may be used to advantage.

The DNA or RNA vectors may be introduced into a cellular host, whereby the expression of the fusion protein can occur. The host may be a primary cell, a cell line, a unicellular microorganism, or the like, where the cell may be modified having an expression construct integrated or transiently present in the cell expressing a secretable form of EA, expressing or over-expressing a protein that the cell does not normally express under the conditions of the assay, not expressing a protein that the cell normally expresses as a result of a knockout, transcription or translation inhibitor, or the like.

The gene encoding the fusion protein will be part of an expression construct. The gene is positioned to be under transcriptional and translational regulatory regions functional in the cellular host. In many instances, the regulatory regions may be the native regulatory regions of the gene encoding the protein that forms the CC, where the fusion protein may replace the native gene. The site of the gene in an extrachromosomal element or in the chromosome may vary as to transcription level. Therefore, in many instances, the transcriptional initiation region will be selected to be operative in the cellular host, but may be from a virus or other source that will not significantly compete with the native transcriptional regulatory regions or may be associated with a different gene from the gene for the CC, which gene will not interfere significantly with the transcription of the fusion protein.

It should be understood that the site of integration of the expression construct, if integrated into a host chromosome, would affect the efficiency of transcription and, therefore, expression of the fusion protein. One may optimize the efficiency of expression by selecting for cells having a high rate of transcription, one can modify the expression construct by having the expression construct joined to a gene that can be amplified and coamplifies the expression construct, e.g. DHFR in the presence of methotrexate, or one may use homologous recombination to ensure that the site of integration provides for efficient transcription. By inserting an insertion element into the genome, such as Cre-Lox at a site of efficient transcription, one can direct the expression construct to the same site. In any event, one will usually compare the enzyme activity from cells in a predetermined environment to cells in the environment being evaluated.

The vector will include the fusion gene under the transcriptional and translational control of a promoter, usually a promoter/enhancer region, optionally a replication initiation region to be replication competent, a marker for selection, and may include additional features, such as restriction sites, PCR initiation sites, an expression construct providing constitutive or inducible expression of EA, or the like. As described above, there are numerous vectors available providing for numerous different approaches for the expression of the fusion protein in a host.

The vector may be introduced into the host cells by any convenient and efficient means, such as transfection, electroporation, lipofection, fusion, transformation, calcium precipitated DNA, etc. The manner in which the vector is introduced into the host cells will be one of efficiency and convenience in light of the nature of the host cell and the vector and the literature has numerous directions for the introduction of a vector into a host cell and the selection of the host cells that have effectively received the vector. By employing expression constructs that allow for selection, e.g. antibiotics, the cells may be grown in a selective medium, where only the cells comprising the vector will survive.

The assay procedure employed is to use the intact cells, either viable or non-viable. Non-viability can be achieved by heat, antibiotics, toxins, etc., which induce mortality while leaving the cells intact. The cells are grown in culture in an appropriate culture medium suitable for the cells and may be grown to confluence or pre-confluence, e.g. 80%. The fusion protein expression construct and other constructs, as appropriate, may be present in the cell integrated into the genome or may be added transiently by the various methods for introducing DNA into a cell for functional translation. These methods are amply exemplified in the literature, as previously described. By employing a marker with the protein reagent for selection of cells comprising the construct, such as antibiotic resistance, development of a detectable signal, etc., cells in culture comprising the fusion protein can be separated from cells in which the construct is absent. Once the fusion protein is being expressed, the environment of the cells may be modified, as appropriate.

Candidate compounds may be added, changes in the culture medium may be created, other cells may be added for secretion of factors or binding to the transformed cells, viruses may be added, or the like. Given sufficient time for the environment to take effect and/or taking aliquots of the culture at different time intervals, the medium may be aspirated off or allowed to incubate to permit the protease to cleave the fusion protein, and then assayed with an assay cocktail comprising EA and enzyme substrate and the signal from the product read. One can then relate this result to the amount of protease present, particularly by using standards where protease activity is known, for example, in the absence of the candidate compound.

In carrying out the assay, the cell containing mixture may be used or the supernatant aspirated and used as the sample for the assay. After adding to the cell medium the protease and other components associated with the activity of the protease, e.g. buffers to provide the desired pH, the sample mixture is then incubated, conveniently at a controlled temperature, which may include room temperature, for at least 1min, usually at least about 5 min and not more than about 30 min, there being no advantage in unduly extending the incubation period. The number of cells present will generally be in the range of about $10^3$-$10^5$ and the volume of the cell medium will generally be in the range of about 5 to 50 µl.

After this incubation EA is added in a volume of about 5 to 50 µl and the mixture incubated for at least about 5 min, usually at least about 10 min and not more than about 60 min, usually not more than about 45 min. Generally the amount of EA will be at least equal to the highest concentration of the ED anticipated to be formed, usually in excess, generally more than about 1000-fold excess, more usually not more than about 10000-fold excess. At this time about 5 to 50 µl of a substrate providing a detectable signal is added, where the substrate is in substantial excess of the amount that will be turned over in the assay. Illustrative substrates, many of which are commercially available, include dyes and fluorescers, such as X-gal, CPRG, 4-methylumbelliferonyl β-galactoside, resorufin β-galactoside, Galacton Star (Tropix, Applied Biosystems). The procedure follows the conventional procedure for other analytes described in the scientific and patent literature. See, for example, U.S. Pat. Nos. 4,708,929 and 5,120,653, as illustrative. The assay mixture may then be read at a specific time, e.g. 1-10 min, or as a rate, taking readings at specific intervals. With a chemiluminescent readout, the signal may be integrated for a time period of from 0.1 s to 1 min.

The following examples are intended to illustrate but not limit the invention.

EXPERIMENTAL

Materials:
HEK293 parental cell line
HEK293 IκB-β-galactosidase ED (55 mer) stable transfectant Growth media (DMEM/10% FBS)
Factor Xa, 1 µg/µl stock in water, kept as a −80° C. stock (Roche, Cat. no. 1 585 924)
Factor Xa cleavage buffer, made by adding 10 mg/mL BSA (New England Biolabs) and 0.5 parts 0.2 M $CaCl_2$ to 98.5 parts Dulbecco's PBS (Sigma Cat. no. D8537) BSA is added just prior to use,
EA core buffer (PIPES, 30.24 g/l; NaCl, 23.38 g/l; EGTA, 3.80 g/l; Mg acetate, 2.15 g/l; Tween, 0.5 mL; NaOH, 6.9 g/l; $NaN_3$, 0.95 g/l, pH 6.9
EA reagent (1.8 µM in EA core buffer)
Cell lysis buffer ($KH_2PO_4$, 0.6805 g/l; $K_2HPO_4$, 0.8709 g/l; NaCl, 0.5844 g/l; CHAPS, 10 g/l; pH 6.9 with NaOH)
Chemiluminescent substrate (Tropix, Applied Biosystems Inc.)+Gal-Star+Emerald Enhancer
Plasmid pPL-FXa-$β_2$-AR (or pPL (ED)-FXa (FXa cleavage consensus sequence)-$β_2$-adrenergic receptor (b2-AR))
Gene 6 transfection reagent (Roche Cat. no. 1 815 091

A construct, named pPL-FX-b2AR, was prepared as follows. First, pCMV-PL-N1, a mammalian expression vector for creating N-terminal ED fusion proteins, was created by precise replacement of the EGFP coding sequences in pEGFP-C1 (Clontech) with sequences encoding ED. Next, a XhoI/BamHI DNA fragment encoding the Fxa cleavage site followed by the b2AR was subcloned into the XhoI/BamHI sites of pCMV-PL-N1, creating a fusion of ED-FXa-b2AR. The Fxa-b2AR DNA fragment was obtained by PCR amplification from a b2AR DNA template using PCR primers that introduced a XhoI site and Fxa cleavage site encoding sequences at the 5' end, and a BamHI site at the 3' end. The sequence is described in copending U.S. application Ser. No.: 10/353,908, filed on Jan. 28, 2003, as SEQ ID NO: 6 except that GST is present at one terminus.

Procedure:

In this study the assay procedure was as follows: HEK293 transfectant cells expressing either the cytoplasmic protein IκB-PL (stable transfectant) or PL-FXa-b2AR (transient transfectant) were seeded into two wells each of a 6-well culture dish at a density that gave ~80% confluency following 2 days growth. For transfection, transfection mix was prepared according to the supplier FUGENE, using 0.15 µl FUGENE reagent, 0.05 µg DNA and 5 µl serum free media. The transfected cells were grown in DMEM/10% FBS media for 48 to 72 hours prior to assay.

At this time, culture media above the cells was removed by gentle aspiration. To one set of wells was added 1.0 mL of FXa buffer composed of PBSC/BSA containing 2 ug/mL FXa. To the other was added the same buffer lacking FXa. Reactions were incubated at room temperature for 1 hour. Liquid above the cells (the supernatant fraction) was carefully collected by pipetting and then transferred to individual microfuge tubes. The supernatants were cleared of any cells that might have been carried over in the transfer by two sequential, gentle centrifugations. Fifty microliters of each supernatant fraction was aliquoted in quadruplicate to individual wells of a 96-well assay plate. To these wells was added 80 ul of EA Core Buffer/EA Reagent (3:1). To the cells remaining in the culture wells (the adherent cell fraction) was added 1 mL of PBSC/BSA followed by 1.6 mL of Cell Lysis Buffer/EA Reagent (3:1). The cells were lysed in this solution by pipetting up and down and then 130 µL of each sample was aliquoted in quadruplicate to individual wells of the 96-well assay plate. The assay plate was incubated at 37° C. for 1 hour, after which 30 µL of CL substrate was added per well. The plate was incubated at room temperature protected from light and readings were taken periodically on the Northstar plate reader from 15 minutes to 1 hour following substrate addition. See FIGS. 1a and 1b for results.

In the next study, a 96 well plate is seeded with HEK293 parental cell line; HEK293 IκB-β-galactosidase ED (55 mer) stable transfectant; HEK293 parental cell line transiently transfected with plasmid pPL-FXa-$β_2$-AR, in 100 µl/well. The HEK293 IκB-β-galactosidase ED (55 mer) stable transfectant that was ~50% confluent was treated with trypsin, quenched with media, centrifuged and resuspended in 6 mL fresh media. The solution was 0.764 mL washed cell suspension and 3.23 mL of fresh media. 100 µl aliquots were transferred to the microtiter plate wells, 4 columns by 8 rows. The HEK293 parental cell line mock transformed was treated as above, except that the cell line was ~90% confluent and 4.2 mLs of the cell suspension was diluted with 17.8 mL of media. For transfection, transfection mix was prepared according to the supplier FUGENE, using 0.15 µl FUGENE reagent, 0.05 µg DNA and 5 µL serum free media. For the mock transfected parental cell line, sterile TE buffer was substituted for the DNA.

After seeding the wells, the cells were allowed to grow to ~80% confluence. Serial dilutions of the FXa solution were made and the dilutions added as 50 µl to separate wells of the different HEK293 cells.

The mixtures were then incubated for 1 h10 min at room temperature. To the treated mixtures were then added 80 µl (60 µl of EA cell lysis buffer and 20 µl of EA reagent) of the EA solution to each well followed by mild agitation. The mixtures were then incubated at 37° C./5% $CO_2$ for 1 h followed by removal from the incubator and the addition of 30 µl chemiluminescent substrate, the plate gently agitated and then incubated in the dark with readings taken at periodic intervals with a Northstar plate reader, reading for 90 sec at 15 min. After adjusting the results for whole-cell values as compared to lysed cell values, the data were graphed showing that there was substantially no change in the readings with variation in the concentration of Factor Xa, while the transiently infected cells showed an increase in the readings from 0.01 ng/well to 1000 ng/well of Factor Xa. The results are shown in FIG. 2.

The assay compared the effect of FXa enzyme concentration on the EFC (enzyme fragment complementation with formation of β-galactosidase) activity as observed with relative luminescent units (RLU). Using either PBSC or PBSC/BSA (0.1%) buffer, a difference in about 30000 RLUs was observed over a range in concentration of FXa of about $10^{-3}$ to $10^1$ µg/mL.

Figure 3:
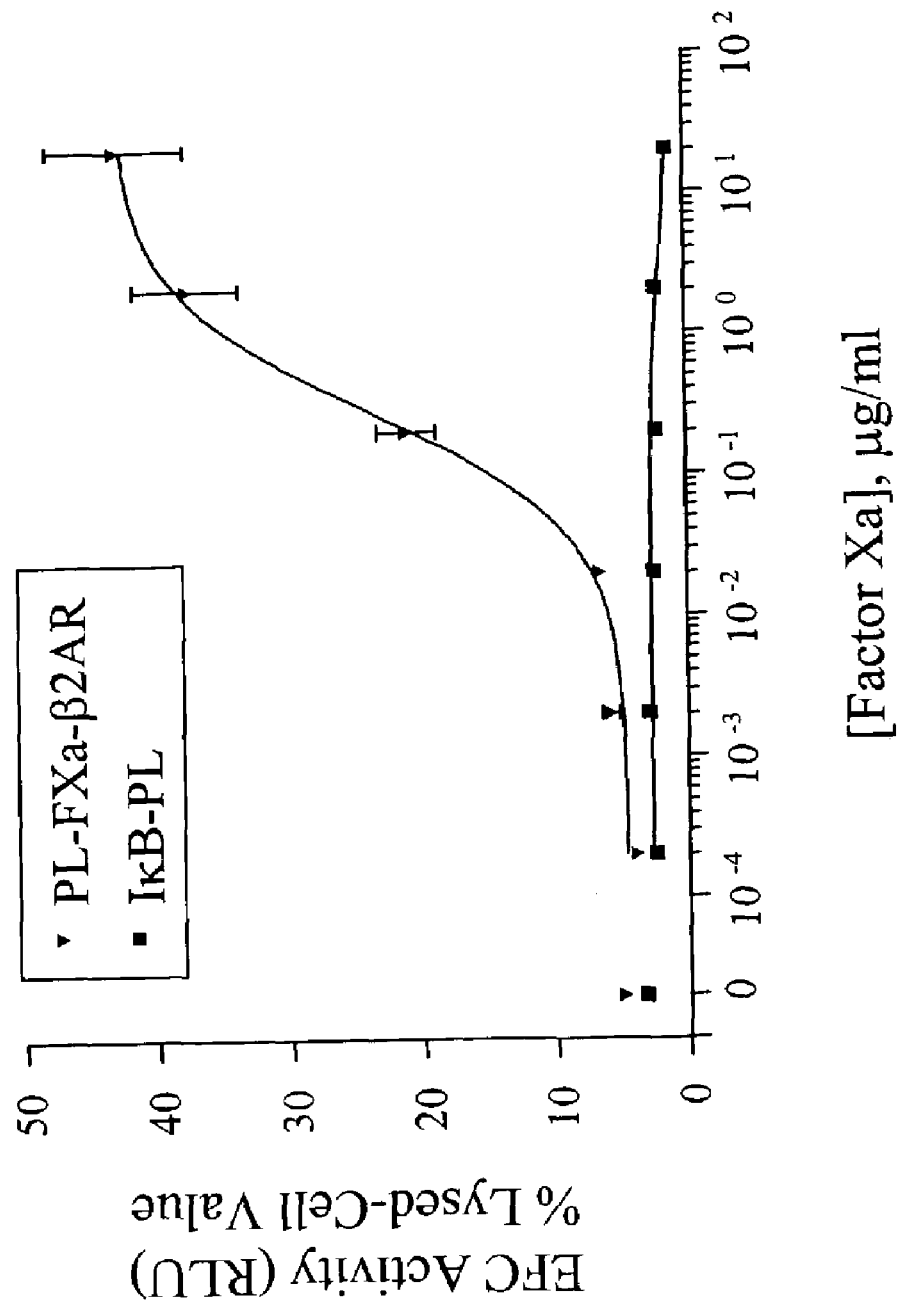
FIG. 3 is a plot of the effect of FXa on lysis of cells.

That FXa does not cause cell lysis was established by using cells transfected with an IκB-ED construct, where only background activity was observed over a concentration range of FXa of about $10^{-4}$ to $2\times10^1$ µg/mL. FIG. 3.

Figure 4:
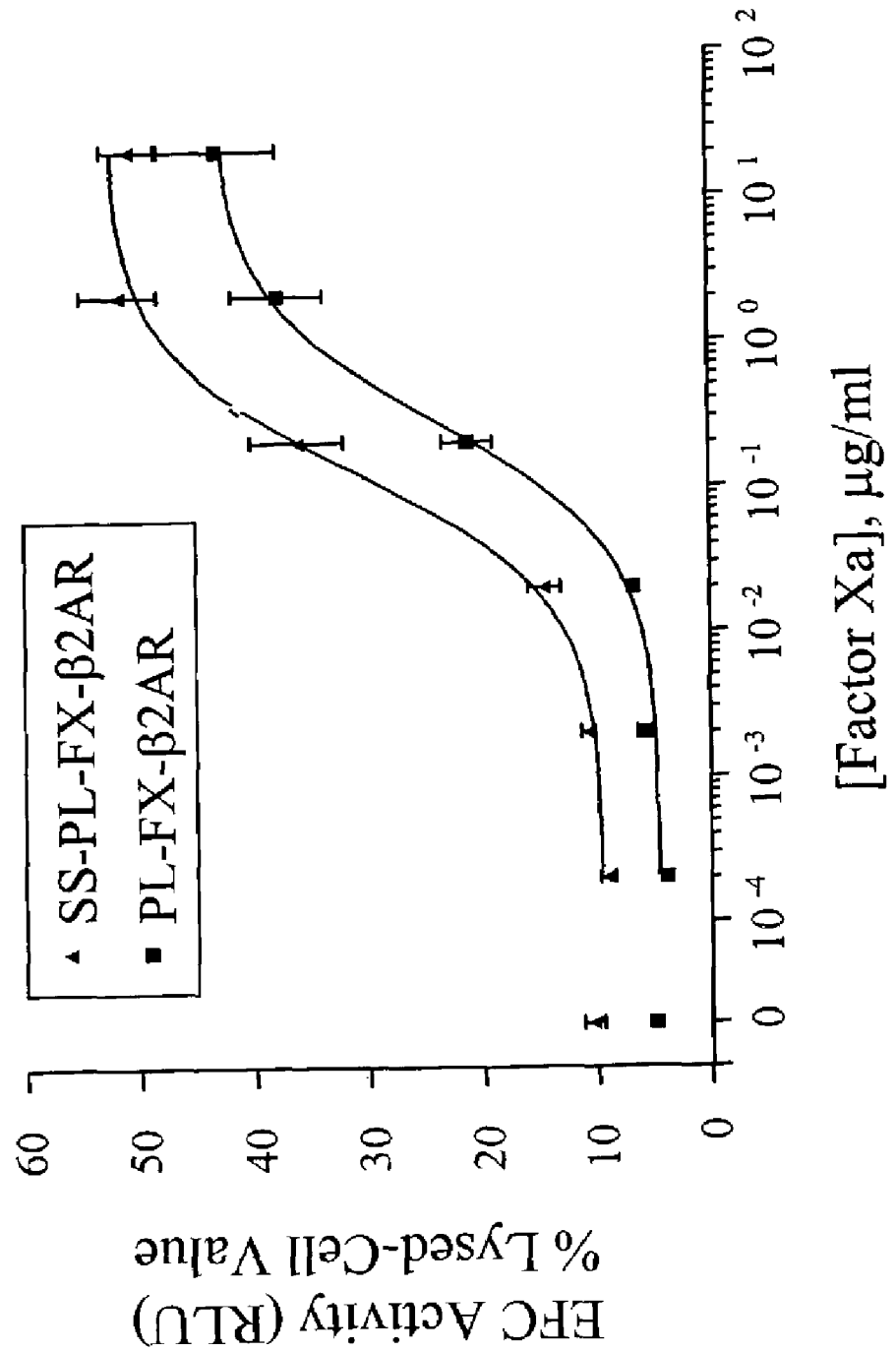
FIG. 4 is a plot of the effect of adding a signal sequence to a genetic construct on the available surface concentration of the expression product of the genetic construct.

It was found that adding the cleavable hemagglutinin signal sequence (MKTIIALSYIFCLVFA) SEQ ID NO: 10 N-terminal to ED further enhanced the transport of the fusion protein to the surface to increase its concentration at the surface. This resulted in a significant increase in signal. See FIG. 4. The signal sequence (SS) expressing DNA construct, pSS-PL-FX-b2AR, was made by replacing the AgeI/XhoI PL fragment of pPL-FX-b2AR with a AgeI/XhoI fragment encoding the cleavable signal sequence followed by PL. The SS-PL fragment was obtained by PCR amplification of PL encoding DNA using pPL-FX-b2AR as a template and PCR primers that introduced an AgeI site and SS sequences 5' of the PL sequences.

In the final study, the effect of an FXa inhibitor was evaluated. The assay was as follows: HEK293 transient transfectant cells expressing Signal Sequence-PL-FXa-b2AR were seeded into individual wells of a 96-well plate at a density that gave ~80% confluency following 2 days growth. Two sets of assay buffers were prepared in PBSC/BSA, one without and one with FXa at 4 µg/mL. Each set represented a 5-fold serial dilution series of the protease inhibitor cocktail Complete Mini, EDTA-free (Roche Cat. No. 1 873 580), with the highest system concentration being 1× according to the manufacturer's instructions. The assay solutions were held at room temperature for 30 minutes after preparation to provide time for inhibition to occur. Culture fluid above the cells was removed by aspiration and replaced by 50 µl of the assay solutions described above, and the plate was incubated at room temperature for 1 hour. 80 µL of EA Core Buffer/EA Reagent (3:1) was added to each well and the plate was maintained at 37° C. for 1 hour. Finally 30 µl of CL substrate was added per well and the plate was incubated at room temperature protected from light. Readings were taken periodically on the Northstar plate reader from 15 minutes to 1 hour following substrate addition. It was shown that over the range of inhibitor concentration of 1× to 1/25× the RLUs varied from about 8,000 to about 11,000, demonstrating that the subject methodology can be used for screening the effect of protease inhibitors in a rapid and convenient assay. The background was shown to be substantially constant in the absence of FXa.

The above results demonstrate that a simple sensitive cellular assay is provided that can be used in a variety of ways, for measuring protease activity, for screening compounds that influence protease activity, directly or indirectly, for detecting diseased states associated with protease activity, and the like. One uses intact cells for measuring the protease activity and by releasing an enzyme fragment that can complex with another fragment to form an active enzyme, one enjoys substantial amplification from each cleavage. The genetic constructs can be readily made and the population of the fusion protein controlled by use of different transcriptional regulatory regions, constitutive or inducible, secretory leaders, surface membrane proteins, etc.

All references referred to in the text are incorporated herein by reference as if fully set forth herein. The relevant portions associated with this document will be evident to those of skill in the art. Any discrepancies between this application and such reference will be resolved in favor of the view set forth in this application.

Although the invention has been described with reference to the above examples, it will be understood that modifications and variations are encompassed within the spirit and scope of the invention. Accordingly, the invention is limited only by the following claims.

What is claimed is:

1. A method for determining target protease activity in a sample, employing a transfected cell comprising a hindered protein reagent, said hindered protein reagent comprising a membrane bound protein component bound to a cell membrane surface, said protein component linked to an enzyme donor fragment of β-galactosidase by a recognition sequence of from 4 to 12 amino acids susceptible to cleavage by said target protease activity to produce an enzyme donor fragment, said cell surface of said hindered protein reagent inhibiting the formation of a complex between said enzyme donor fragment of β-galactosidase and a partner enzyme acceptor fragment of β-galactosidase resulting in a low background signal, wherein cleavage produces a protein reagent fragment active with said enzyme acceptor fragment of said β-galactosidase to produce an active β-galactosidase enzyme resulting in an increase in β-galactosidase enzyme activity, wherein β-galactosidase enzyme activity is related to said target protease activity, said method comprising:

combining said transfected cell, said sample, enzyme acceptor fragment of β-galactosidase and β-galactosidase enzyme substrate for a time sufficient for said target protease activity to cleave said recognition sequence; and measuring the β-galactosidase enzyme activity as an indication of the protease activity.

2. The method according to claim 1, wherein said enzyme donor fragment and said enzyme acceptor fragment are free of complexing fragments and are fragments of said enzyme that independently complex to form an active β-galactosidase enzyme.

3. The method according to claim 1, wherein said enzyme donor fragment and said enzyme acceptor fragment consist of fusion proteins, said enzyme donor fragment comprised of a first binding protein and a first fragment of said β-galactosidase enzyme and said enzyme acceptor fragment comprised of a second binding protein and a second fragment of said β-galactosidase enzyme, wherein said first and second fragments of said β-galactosidase enzyme do not independently complex to form an active enzyme and upon complex formation of said first and second binding proteins an active β-galactosidase enzyme is formed.

4. The method according to claim 3, wherein first and second binding proteins require a supplemental reagent for binding.

5. The method according to claim 1, wherein said protein reagent is anchored to said cell membrane by an amino acid sequence spanning said cell membrane.

6. The method according to claim 1, wherein said enzyme donor is of from about 37 to 120 amino acids.

7. The method according to claim 1, wherein said recognition sequence is within 50 amino acids of said enzyme donor.

8. A method for determining protease activity in a sample, employing a transfected cell comprising a hindered protein reagent, said hindered protein reagent comprising a membrane bound protein component bound to an intact cell membrane surface hindering entity, said protein component linked to an enzyme donor fragment of β-galactosidase by an amino acid recognition sequence of from 4 to 12 amino acids specifically susceptible to cleavage by said target protease activity to produce an enzyme donor fragment, said membrane cell surface hindering entity of said hindered protein reagent inhibiting the formation of a complex between said enzyme donor fragment of β-galactosidase and a partner enzyme acceptor fragment of β-galactosidase resulting in a low background signal, wherein cleavage produces a protein reagent fragment active with said enzyme acceptor fragment of β-galactosidase to produce an active β-galactosidase resulting in an increase in β-galactosidase activity, wherein β-galactosidase activity is related to said protease activity, said method comprising:

combining said transfected cell, said sample, enzyme acceptor fragment of said β-galactosidase and β-galactosidase substrate for a time sufficient for said protease activity to cleave said amino acid sequence; and measuring the β-galactosidase activity as an indication of the protease activity.

9. The method according to claim 8, wherein said amino acid recognition sequence is within 50 amino acids of said enzyme donor.

10. The method according to claim 8, wherein said protease is a serine/threonine hydrolase.

11. The method according to claim 8, wherein said protease is a metalloproteinase.

* * * * *